United States Patent [19]
Rogalsky et al.

[11] Patent Number: 5,197,483
[45] Date of Patent: Mar. 30, 1993

[54] TISSUE DISAGGREGATOR

[76] Inventors: Vitaly Rogalsky; Alena Rogalsky, both of 186 Pinehurst Ave., New York, N.Y. 10033

[21] Appl. No.: 562,807

[22] Filed: Aug. 6, 1990

[51] Int. Cl.$^5$ .............................................. A61B 10/00
[52] U.S. Cl. ................................. 128/749; 241/169.2
[58] Field of Search .................... 128/749, 752, 758; 604/317–321; 241/167.1, 169.2

[56] References Cited
U.S. PATENT DOCUMENTS 3,224,434 12/1965 Molomu et al. ................... 128/749
3,298,411 1/1967 Rosett ................................ 128/749
4,393,879 7/1983 Milgrom ............................ 128/758
4,715,545 12/1987 Hanifl ................................ 128/749

Primary Examiner—Max Hindenburg
Attorney, Agent, or Firm—Ilya Zborovsky

[57] ABSTRACT

A device for disaggregating tissues comprises a pestle having a working end provided with a net, and at least one additional net communicating with a source of vacuum, so that a tissue placed on the additional net can be desegregated by rubbing the net of the pastle against the additional net under vacuum pulling separated tissues through the additional net.

7 Claims, 1 Drawing Sheet

TISSUE DISAGGREGATOR

BACKGROUND OF THE INVENTION

The present invention relates to disaggregator for tissues, especially to fermentless disaggregators for tissues. Disaggregators for tissues are well known and used in great varities. The known disaggregators for tissues can be further improved in the sense of improving the efficiency of the disaggregation of tissues.

SUMMARY OF THE INVENTION

Accordingly, it is an object of the present invention to provide a disaggregator for tissues which is a further improvement of the existing disaggregators.

In keeping with these objects and with others which will become apparent hereinafter, one feature of the present invention resides, briefly stated, in a device for disaggregation of tissues which comprises a pestle having a working end and provided with a net on its end, and at least one additional net connected with a vacuum source.

When the device for disaggregation of tissues is designed in accordance with the present invention, the efficiency of the process is significantly improved.

In accordance with another feature of the present invention, the additional net can be connected with a vacuum vessel.

Still another feature of the present invention is that several additional nets are arranged at a distance from one another.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

Figure 1:
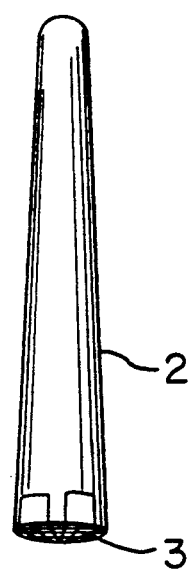
FIG. 1 is a perspective view of a device for disaggregating tissues in accordance with the present invention.
Figure 2:
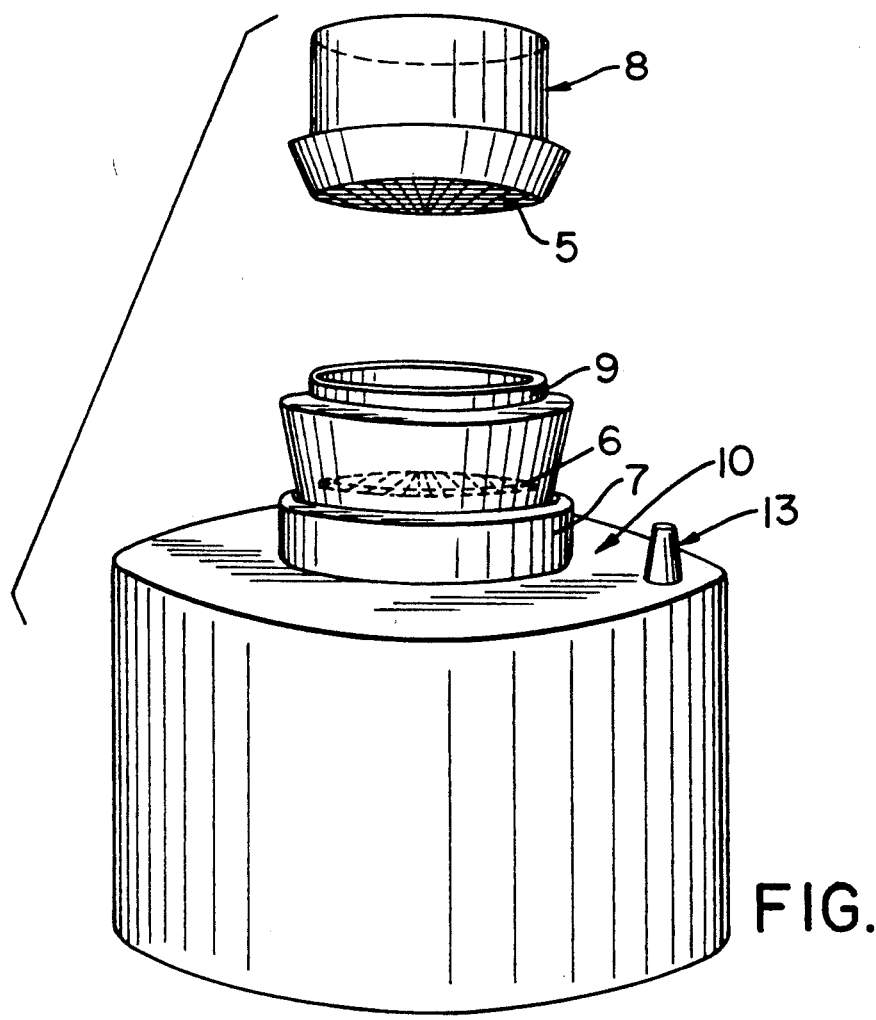
FIG. 2 is a cross-section of the inventive device for disaggregating tissues.

A device for disaggregating tissues has a pestle which is identified as a whole with reference numeral 1. The pestle 1 has a main part 2 and a net 3 provided at a working end of the main part. It is to be understood that a small recess 4 is formed in the working end of the pestle. 1 and the net 3 is arranged on the edge of the end of the pestle.

At least one additional net 5 is further provided in the opposite part of the inventive device. In accordance with an advantageous feature of the present invention several such additional nets can be provided in the inventive device and the size of the openings in the nets reduce in direction of the upper net 5 to the lower net 6. For example, the size of the pores in the net 5 can be substantially 0.3 mm, while the size of the pores in the net 6 can be 10-50 microns. The pores in the last net can be even 10-40 microns.

As can be seen from the drawings, the nets are arranged in a cylinder identified as a whole with reference numeral 7. The cylinder can be formed as a single cylindrical body. However, as shown in the drawings, it can be composed of separate cylindrical elements 8 and 9 arranged over one another, for example in a nesting arrangement. The lower end of the cylinder 9 is introduced into a vacuum vessel 10. For example, the lower end of the cylinder 7 can extend through a central opening of the vacuum vessel. The vessel 10 has a passage 13 connectable with a not shown vacuum source.

In operation, pieces of tissues of the size of for example 0.3-0.5 mm are placed on the upper net 5 and softly rubbed with the net 3 of the pestle 1. In this process the separated tissues are flushed by a culture medium, so that the tissues are accumulated in the vessel. A vacuum applied to the vessel 10 aspirates the pieces of tissues through the nets 5 and 6 into the interior of the vessel 10. The net on the pastle 1, and "pulling" of the pieces of tissues through the successively reducing pores of the additional nets under a controllable vacuum provide for very soft conditions for seperating the tissues from one another and forming a suspension of individual floating tissues.

For further improvement of the disaggregating of tissues, it is recommended to pass again the tissues through the nets.

It will be understood that each of the elements described above, or two or more together, may also find a useful application in other types of constructions differing from the types described above.

While the invention has been illustrated and described as embodied in a device for desegregating of tissues, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

The pestle with the net at its end provides for softer conditions of cell separation and as a result more cells retain their vitality. The use of two or more nets with reducing size of openings also leads to higher yield of the cells, while fibers are retained on the nets.

What is desired to be protected by Letters Patent is set forth in the appended claims.

We claim:

1. A device for disaggregating tissues, comprising a pestle having a working end provided with a net; and at least one additional net communicating with a source of vacuum, so that a tissue placed on said additional net can be desegregated by rubbing said net of said pestle against said additional net under vacuum pulling separated tissues through said additional net.

2. A device as defined in claim 1; and further comprising at least one second such additional net; said additional nets being spaced from one another and having pores of a different size.

3. A device as defined in claim 2; and further comprising a holding element arranged o hold said additional nets one above the other, a lower one of said additional nets having pores of a size which is smaller than a size of pores of an upper one of said additional nets.

4. A device as defined in claim 2; and further comprising a holder for holding said additional nets, said holder being formed as an integral member.

5. A device as defined in claim 2; and further comprising a holder for holding said additional nets, said holder including at least two holding parts each holding a respective one of said additional nets, said holding parts being nestable in one another.

6. A device as defined in claim 1; and further comprising a holding element arranged to hold said additional net.

7. A device as defined in claim 1; and further comprising a vacuum vessel, said additional net being connected with said vacuum vessel.

* * * * *